(12) United States Patent
Ray

(10) Patent No.: US 8,608,719 B2
(45) Date of Patent: Dec. 17, 2013

(54) DISPOSABLE PARTIALLY FLEXIBLE SURGICAL FLUID CONTAINER

(76) Inventor: Stephen P. Ray, Trevor, WI (US)

( * ) Notice: Subject to any disclaimer, the term of this patent is extended or adjusted under 35 U.S.C. 154(b) by 0 days.

(21) Appl. No.: 13/461,924

(22) Filed: May 2, 2012

(65) Prior Publication Data

US 2013/0296817 A1   Nov. 7, 2013

(51) Int. Cl.
*A61B 19/00* (2006.01)
*A61F 5/44* (2006.01)
*A61M 1/00* (2006.01)

(52) U.S. Cl.
USPC ............ 604/356; 604/355; 604/357; 604/317

(58) Field of Classification Search
USPC .................. 604/355–357, 317–327; 222/511, 222/516–517; 4/144.1, 144.3
See application file for complete search history.

(56) References Cited

U.S. PATENT DOCUMENTS

| 4,068,034 | A |   | 1/1978 | Segawa |
| 4,392,594 | A |   | 7/1983 | Swett |
| 4,795,435 | A | * | 1/1989 | Steer .............................. 604/355 |
| 4,947,896 | A | * | 8/1990 | Bartlett .......................... 600/187 |
| 5,045,076 | A |   | 9/1991 | Pierce |
| 5,618,278 | A | * | 4/1997 | Rothrum ........................ 604/356 |
| 5,915,628 | A |   | 6/1999 | Kreizel |
| 6,155,620 | A | * | 12/2000 | Armstrong ....................... 294/57 |
| 7,195,617 | B2 | * | 3/2007 | Papendick et al. ............. 604/317 |
| 7,306,120 | B2 |   | 12/2007 | Hughes |
| 8,382,730 | B2 | * | 2/2013 | Tauer ............................. 604/317 |
| 2009/0159607 | A1 |   | 6/2009 | Kratzer |
| 2012/0143241 | A1 |   | 6/2012 | Ray |

FOREIGN PATENT DOCUMENTS

WO  PCT/US2013/037714   4/2013

* cited by examiner

*Primary Examiner* — Philip R Wiest
*Assistant Examiner* — Benjamin Klein
(74) *Attorney, Agent, or Firm* — Lesavich High-Tech Law Group, P.C.; Stephen Lesavich

(57) ABSTRACT

A disposable partially flexible surgical fluid container. The apparatus includes a triangular shaped portion comprising a rigid fluid collection portion for storing fluids, a flexible sealing portion for creating a seal for catching surgical fluids, an ergonomic handle portion for grasping and holding and a horizontal bottom portion for standing the apparatus upright when placed on a flat surface. The flexible sealing portion includes a flexible, conformable material for conforming to flat, convex and concave wound surfaces and creating a seal between the flexible pouring portion and the wound surfaces to prevent leaking of collected surgical fluids (e.g., irrigation fluids, etc.) during a surgery.

17 Claims, 8 Drawing Sheets

SIDE VIEW

SIDE VIEW

TOP VIEW

CROSS SECTION VIEW

TOP VIEW
CONVEX WOUND

TOP VIEW
CONCAVE WOUND

SIDE VIEW

TOP VIEW
CONVEX WOUND the present invention will be more readily apparent from the following detailed description. The detailed description proceeds with references to the accompanying drawings.

DISPOSABLE PARTIALLY FLEXIBLE SURGICAL FLUID CONTAINER

FIELD OF THE INVENTION

This invention relates to surgical instruments. More specifically, it relates to a disposable partially flexible surgical fluid container.

BACKGROUND OF THE INVENTION

It is common practice to use irrigation fluids (e.g., 0.9% or other concentration sodium chloride, lactated Ringer's solutions, etc.) to wash out debris, blood, tissue, fat or unwanted body fluids during surgeries on human. Antibiotic irrigation fluids are also used during surgery to prevent infection.

Irrigation fluids used to irrigate/wash a body cavity during a surgery include moderate (500 mls to 1000 mls) to volumes large volumes including those greater than 2000 mls, are routinely used. There are several problems associated with using irrigation fluids during surgery.

One problem is that during a surgical procedure it is necessary to irrigate the wound cavity or surface to clear away blood and tissue particles. It is usually necessary to hold a container up to the wound edge to keep the irrigating solution from flowing over the wound edge and running down the surfaces and onto the drapes and then the floor.

Another problem is that is a very common practice is to use a kidney basin with a thin rigid lip to the wound edge in hopes of catching the fluid. Kidney basins have a standard size and shape (i.e., a kidney shape), have rounded ends. The surgeon or assistant presses the most appropriate rigid surface against the wound and tries to get a seal so the fluid will run from the wound edge into the basin and is then suctioned or discarded.

Another problem is that due to the many surface contours of the bony skeleton and the soft tissue of a human body and differences in patient physical size and wound opening sizes, it is usually very difficult to get a good seal because of the kidney basins fixed size, shape and edges. As a result body fluids, particulate matter and saline spill out of the wound onto other parts of the patient, the operating room table, the surgical staff and the floor. The shape of the basin also makes it very difficult to hold easily while applying pressure to attempt to get a seal with the wound edge.

Thus, it is desirable to solve some of the many problems associated with collecting irrigation fluids used for surgery on humans during a surgery.

SUMMARY OF THE INVENTION

In accordance with preferred embodiments of the present invention, some of the problems associated with fluids used during a surgery overcome. A disposable partially flexible surgical fluid container is presented.

The apparatus includes a triangular shaped portion comprising a rigid fluid collection portion for storing fluids, a flexible sealing portion for creating a seal for catching surgical fluids, an ergonomic handle portion for grasping and holding and a horizontal bottom portion for standing the apparatus upright when placed on a flat surface. The flexible sealing portion includes a flexible, conformable material for conforming to flat, convex and concave wound surfaces and creating a seal between the flexible pouring portion and the wound surfaces to prevent leaking of collected surgical fluids (e.g., irrigation fluids, etc.) during a surgery.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein.

DETAILED DESCRIPTION OF THE INVENTION

Figure 1:
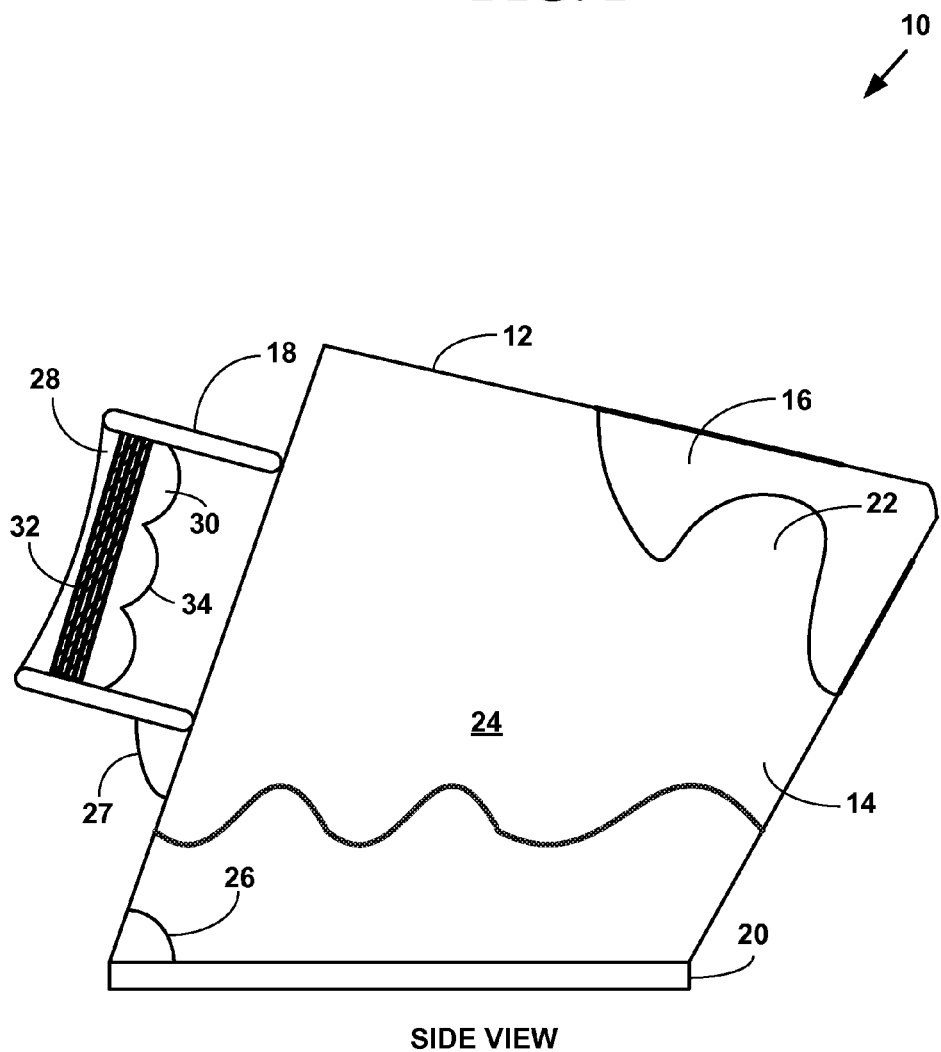
FIG. 1 is a block diagram illustrating a side view of a disposable partially flexible surgical fluid container apparatus.

FIG. 1 is a block diagram illustrating a side view 10 of a disposable partially flexible surgical fluid container apparatus 12.

Figure 2:
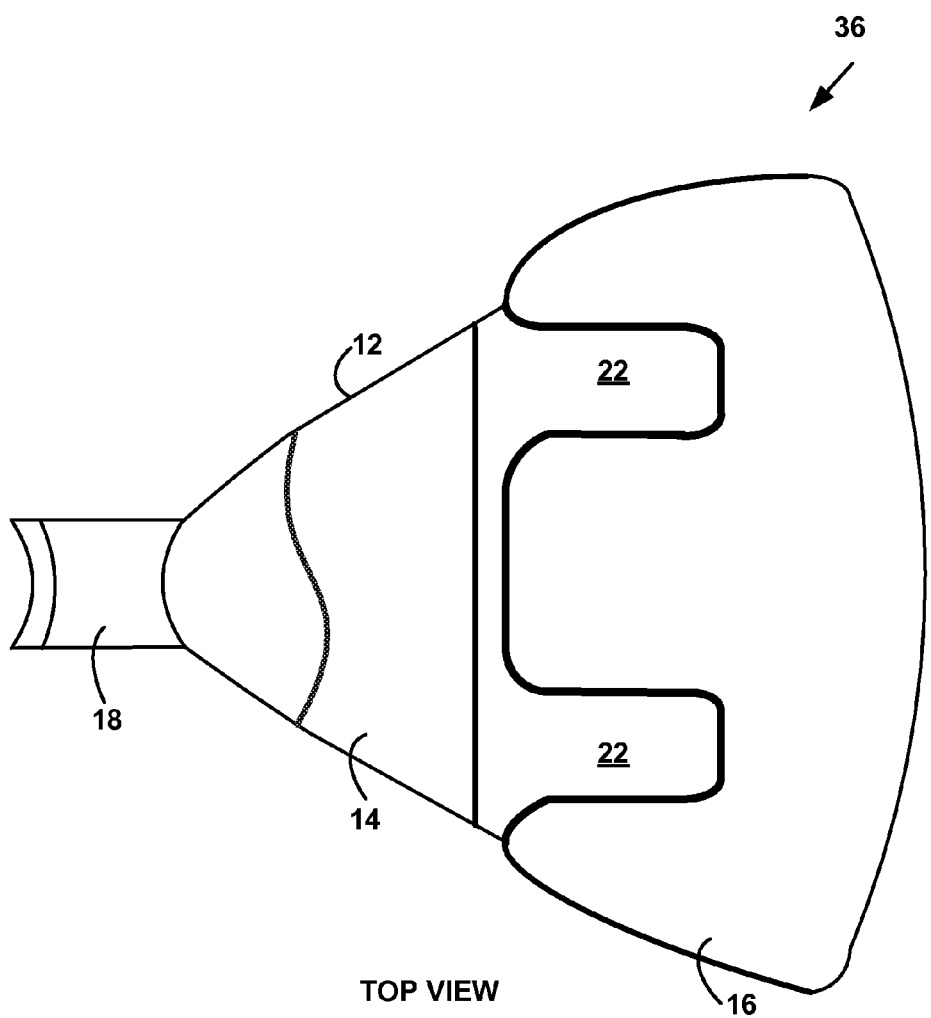
FIG. 2 is a block diagram illustrating a top view of the disposable partially flexible surgical fluid container apparatus.

FIG. 2 is a block diagram illustrating a top view 36 of the disposable partially flexible surgical fluid container apparatus 12.

The apparatus 12 includes a triangular shaped portion comprising a rigid fluid collection portion 14 for storing collecting fluids, a flexible sealing portion 16 for creating a seal for catching surgical fluids, a moveable ergonomic handle portion 18 for grasping and holding and a horizontal bottom portion 20 for standing the apparatus 12 upright when placed on a flat surface.

However, the present invention is not limited to components and more, fewer and other components can be used to practice the invention.

It has been determined experimentally that the triangular shape of the apparatus 12 is one optimal shape for pushing the apparatus 12 forward and applying a steady forward force under a wound during a surgery and engaging the flexible sealing portion 16 for creating a seal for catching surgical fluids during the surgery. However, the present invention is not limited to this shape and other shapes for the apparatus 12, can be used to practice the invention.

The rigid fluid collection portion 14 includes a rigid material for collecting surgical fluids from a wound during a surgery. In one embodiment, the rigid fluid collection portion includes plural rigid protrusions 22 protruding into the flexible sealing portion 16 providing additional surfaces for applying pressure and control in holding the flexible catching portion against a wound surface.

FIG. 2 illustrates the plural rigid protrusions 22 oriented at a 90 degree angle to a front surface of the rigid fluid collection portion 16. However, the present invention is not limited to this angle and other angles can be used to practice the invention.

Returning to FIG. 1, the rigid fluid collection portion 14 includes plural trapezoid shaped sides 24 oriented at a predetermined angle 26 from the horizontal bottom portion 20. In another embodiment, the plural rigid protrusions 22 are not included on the rigid fluid collection portion 14. However, the present invention is not limited to this these embodiments and other embodiments can be used to practice the invention.

In one embodiment, the rigid fluid collection portion 14 holds about 640 fluid ounces (about 1000 mls or 1 liter) of solution. In another embodiment, the rigid fluid collection portion 14 holds about 1280 fluid ounces (about 2000 mls or 2 liters). In another embodiment, the rigid fluid collection portion 14 holds about 320 fluid ounces (about 500 mls). However, the present invention is not limited to these embodiments and larger, smaller and different capacity fluid collection portions 14 may be used to practice the invention.

In one embodiment, rigid fluid collection portion 14 is created from a rigid plastic including Polyetherimide, Polyimide other thermosetting polyimides, other plastics and/or composite materials.

However, the present invention is not limited to these materials and other materials can be used for the rigid fluid collection portion 14 to practice the invention.

"Polyetherimide" (PEI) is an amorphous, amber-to-transparent thermoplastic with characteristics similar to the related plastic PEEK. Polyether ether ketone (PEEK) is a colorless organic polymer thermoplastic Relative to PEEK, PEI is cheaper, but less temperature-resistant and lower in impact strength.

For example, commercially, ULTEM is a family of PEI products manufactured by SABIC. ULTEM resins are used in medical and chemical instrumentation due to their heat resistance, solvent resistance and flame resistance.

"Polyimide" (PI) is a polymer of imide monomers. Such imide monomers include pyromellitic dianhydride and 4,4'-oxydianiline and others. Polyimide materials are lightweight, flexible, resistant to heat and chemicals. Polyimide parts are not affected by commonly used solvents and oils, including hydrocarbons, esters, ethers, alcohols and freons. They also resist weak acids.

"Thermosetting polyimides" are known for thermal stability, good chemical resistance, excellent mechanical properties. Normal operating temperatures for such polymides range from cryogenic with temperatures below about −238° F. (−150° C.) to those exceeding about 500° F. (260° C.).

"Composite materials" are engineered or naturally occurring materials made from two or more constituent materials with significantly different physical or chemical properties which remain separate and distinct at the macroscopic or microscopic scale within the finished structure. Common polymer-based composite materials, include at least two parts, a substrate (e.g., fibers, etc.) and a resin.

The composite materials include "Fiber-reinforced polymers" (FRP) including thermoplastic composites, short fiber thermoplastics, long fiber thermoplastics or long fiber-reinforced thermoplastics. There are numerous thermoset composites, but advanced systems usually incorporate aramid fiber and carbon fiber in an epoxy resin matrix. The composite materials also include carbon/carbon composite materials with carbon fibers and a silicon carbide matrix.

However, the present invention is not limited to these materials and other materials can be used to practice the invention.

In one embodiment, the flexible sealing portion 16 is permanently attached to the rigid fluid collection portion 14.

The flexible sealing portion 16 includes a flexible, conformable material for conforming to flat, convex and concave wound surfaces and creating a seal between the flexible pouring portion and the wound surfaces to prevent leaking of collected fluids.

The flexible conformable material varies in thickness from a first greater thickness on a first part attached to the rigid fluid collection portion 14 and a second lesser thickness a second part for conforming to flat, convex and concave wound surfaces.

In one embodiment, the flexible conformable material varies in thickness from about ten milliliters (ml) (about 0.39 inches) at the first greater thickness part to about one ml (about 0.039 inches) at the second lesser thickness part. However, the present invention is not limited to these thicknesses and other materials can be used to practice the invention.

Figure 3:
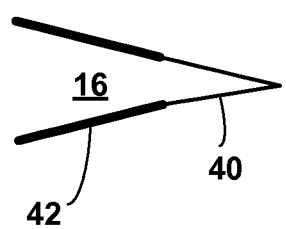
FIG. 3 is a block diagram illustrating a cross section view of a flexible sealing portion of the disposable partially flexible surgical fluid container apparatus.

FIG. 3 is a block diagram illustrating a cross section view 38 of the flexible sealing portion 16 of the disposable partially flexible surgical fluid container apparatus 12. The thickness varies from the greater thickness part 40 to the second lesser thickness part 42 to form a sharp edge 44. The greater thickness part 40 provides additional stability and the lesser thickness part 42 provides sharp edge 44 for creating good seal against flat, convex and concave wound surfaces.

In one embodiment, the flexible sealing portion 16 is constructed from PolyVinyl Chloride (PVC) polyethylene, polypropylene, very low-density polyethylene (VLDPE), linear low-density polyethylene (LLDPE) Flexible polypropylene (FPP), Ethylene interpolymer alloy (EIA), EPDM (ethylene propylene diene monomer), composite materials and/or other flexible materials. However, the present invention is not limited to these materials and other materials can be used to practice the invention.

Polyvinyl chloride (PVC) is durable, cheap, and easily worked into membranes. Polyvinyl chloride is produced by polymerization of a monomer, vinyl chloride (VCM). PVC's are relatively low cost, biological and chemical resistance and very workable into membranes.

Very low-density polyethylene (VLDPE) and linear low-density polyethylene (LLDPE) overcome the shortcomings of other polyethylenes (e.g., high density polyethylene (HDPE), etc. in terms of flexibility. These are less crystalline forms of polyethylene which result in increased flexibility and a membrane less conducive to brittle stress cracking.

Flexible polypropylene (FPP) is produced in both unreinforced (PPU) and reinforced (PPR) form to provide a choice in terms of tensile behavior.

Ethylene interpolymer alloy (EIA) is an alloy of PVC resin with a special ethylene interpolymer that results in a flexible plastic-free material. EIA geomembranes maintain the advantages of PVC but have a high degree of durability and chemical resistance.

EPDM (ethylene propylene diene monomer) was developed from butyl rubber and exhibits excellent elongation characteristics.

However, the present invention is not limited to these materials and other materials can be used to practice the invention.

In another embodiment, the flexible sealing portion 16 is removeable/re-attachble from/to the rigid fluid collection portion 14.

Figure 4:
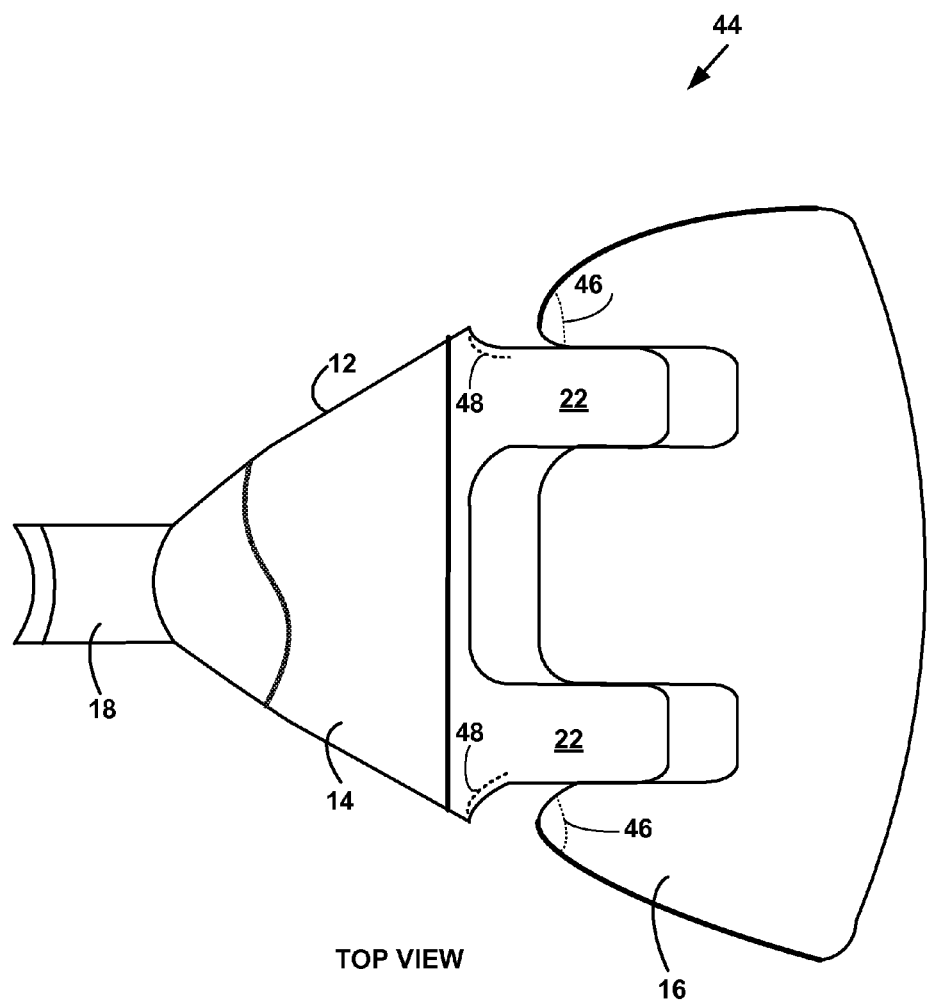
FIG. 4 is a block diagram illustrating another top view of the disposable partially flexible surgical fluid container apparatus with a removeable/re-attachble flexible sealing portion.

FIG. 4 is a block diagram illustrating another top view 44 of the disposable partially flexible surgical fluid container apparatus 12 with a removeable/re-attachble flexible sealing portion 16. In such an embodiment the removeable/re-attachble flexible sealing portion 16 includes plural different sizes and different shapes for different types of wounds and/or different types of surgeries. For example, a smaller removeable/re-attachble flexible sealing portion 16 may be used for a surgery with a small wound and a larger removeable/re-attachble flexible sealing portion 16 may be used for a surgery with larger wound. The different shapes included additional concave, convex and/or flat shaped portions. However, the present invention is not limited to these embodiments and other materials can be used to practice the invention.

In such an embodiment, the connection and attaching and removing the flexible sealing portion 16 includes a snap connection means and/or a magnetic connection means and/or other connection means.

FIG. 4 illustrates a snap connection means. A "snap connection means" includes one or more bulbous protrusions 46 on the flexible sealing portion 16 that engage one or more bulbous depressions 48 on the rigid fluid collection portion 14. In another embodiment, the snap connection means includes one or more bulbous protrusions 46 on the flexible sealing portion 16 that engage one or more bulbous depressions 48 rigid fluid collection portion 14 (Not illustrated in FIG. 4).

A "magnetic connection means" includes small magnetic components placed on the on the flexible sealing portion 16 for connecting to the rigid fluid collection portion 14. In such an embodiment only a small portion of the connection component for connecting and the rigid fluid collection portion 14 and the flexible sealing portion 16 include magnetic components since large magnetic fields may detrimental to other electronic equipment and metal instruments used during the surgery. For example, only portions of to the rigid fluid collection portion 14 and the flexible sealing portion 16 are magnetic materials and/or may be coated with magnetic materials.

Various other types connection means can be used to keep the first attached component and the second moveable component 44 connected. However, the present invention is not limited to the embodiments described and more, fewer and other equivalent connection means embodiments can also be used to practice the invention.

"Ergonomics" is a good 'fit' between a user, equipment and their environments. Ergonomics takes account of the user's capabilities and limitations in seeking to ensure that tasks, functions, information, safety and the environment suit each user. Ergonomic devices are produced to lower a number of or prevent injuries from using the device.

Returning to FIG. 1 the ergonomic handle portion 18 is attached to the rigid fluid storage portion 16 at a pre-determined angle 27 and comprises a pre-determined pattern specifically sized and shaped for comfortable gripping by a human hand, the pre-determined angle allowing accurate collecting of fluids into the flexible catching portion from a wound during the surgery.

The ergonomic handle portion 18 includes a top surface 28 and a bottom surface 30. The pre-determined fixed angle 27 is selected for optimal gripping comfort as well as optimal fluid pouring/dispensing capabilities. In one embodiment, the pre-determined fixed angle 27 is fixed at one angle at about ten to about forty degrees. However, the present invention is not limited to such an embodiment and more, fewer or other types of handle attachment angles can be used to practice the invention.

In another embodiment, the ergonomic handle portion 18 is manually moveable and configurable by a user from angles of about one to about forty-five degrees. However, the present invention is not limited to such an embodiment and more, fewer or other types of handle attachment angles can be used to practice the invention.

The ergonomic handle portion 18 comprises a pre-determined pattern specifically sized and shaped for comfortable gripping by a human hand, the pre-determined angle allowing accurate collection of fluids from the wound during the surgery.

The ergonomic handle portion 18 is designed for right or left-handed gripping and allows for easy pouring and dispensing control.

The top surface 28 includes a pre-determined pattern of protrusions 32 orientated along an axis of the top surface. The protrusions 32 help provide a surface that can be grasped with slippery surgical gloves covered with blood and/or other fluids.

In one embodiment, the protrusions 32 are circular and/or oval and/or trapezoidal in shape. The protrusions prevent slipping during a surgery. The pre-determined pattern includes protrusions 32 of a same shape or combinations thereof of different shapes. However, the present invention is not limited to such an embodiment and more, fewer or other types of protrusions can be used to practice the invention.

In one embodiment, the top surface 28 includes a pre-determined cross-hatch pattern 32 of protrusions. (Illustrated in FIG. 1). The cross-hatch pattern 32 includes a pre-determined pattern of two or more sets of intersecting parallel protrusions. One or more of the sets of intersecting parallel lines protrude up and away from the top surface. Cross-hatch patterns are often used on filing tools used in the construction industry. The protrusions on the cross-hatch pattern 32 provide a non-slip gripping surface on the handle 18.

In one embodiment, the cross hatch protrusions 32 are square, rectangular, circular and/or oval and/or trapezoidal in shape. The pre-determined pattern includes protrusions of a same shape or combinations thereof of different shapes. However, the present invention is not limited to such an embodiment and more, fewer or other types of protrusions can be used to practice the invention.

In another embodiment, surfaces of the handle 18 other than the bottom surface 30 of the ergonomic handle portion 18 includes the cross-hatching 32 pattern to provide additional gripping and non-slipping functionality. However, the present invention is not limited to such an embodiment and more, fewer or other types of gripping/non-slip surfaces can be used to practice the invention.

Returning to FIG. 1 the ergonomic handle portion 18 has a bottom surface 30 in a "wave" pattern 34 specifically sized and shaped to be gripped by a human hand. The wave pattern 34 includes plural wave crests and wave depressions between the wave crests for engaging human fingers comfortably for gripping.

In another embodiment, the ergonomic handle portion 18 includes a twisted spiral shaped for engaging human fingers comfortably for gripping (Not illustrated in FIG. 1).

However, the present invention is not limited to such an embodiment and more, fewer or other types of gripping shapes and patterns can be used to practice the invention.

In one embodiment, the horizontal bottom portion 20 includes a weighted portion for standing the apparatus upright when placed on a flat surface when filled with fluids collected from a surgery. In one embodiment, the weighted portion includes a metal, ceramic plastic, rubber and/or composite material. The weight portion provides additional stability to the apparatus 12 when it is filled with fluids collected during a surgery. However, the present invention is not limited to such an embodiment and more, fewer or other types of embodiments can be used to practice the invention.

Figure 5:
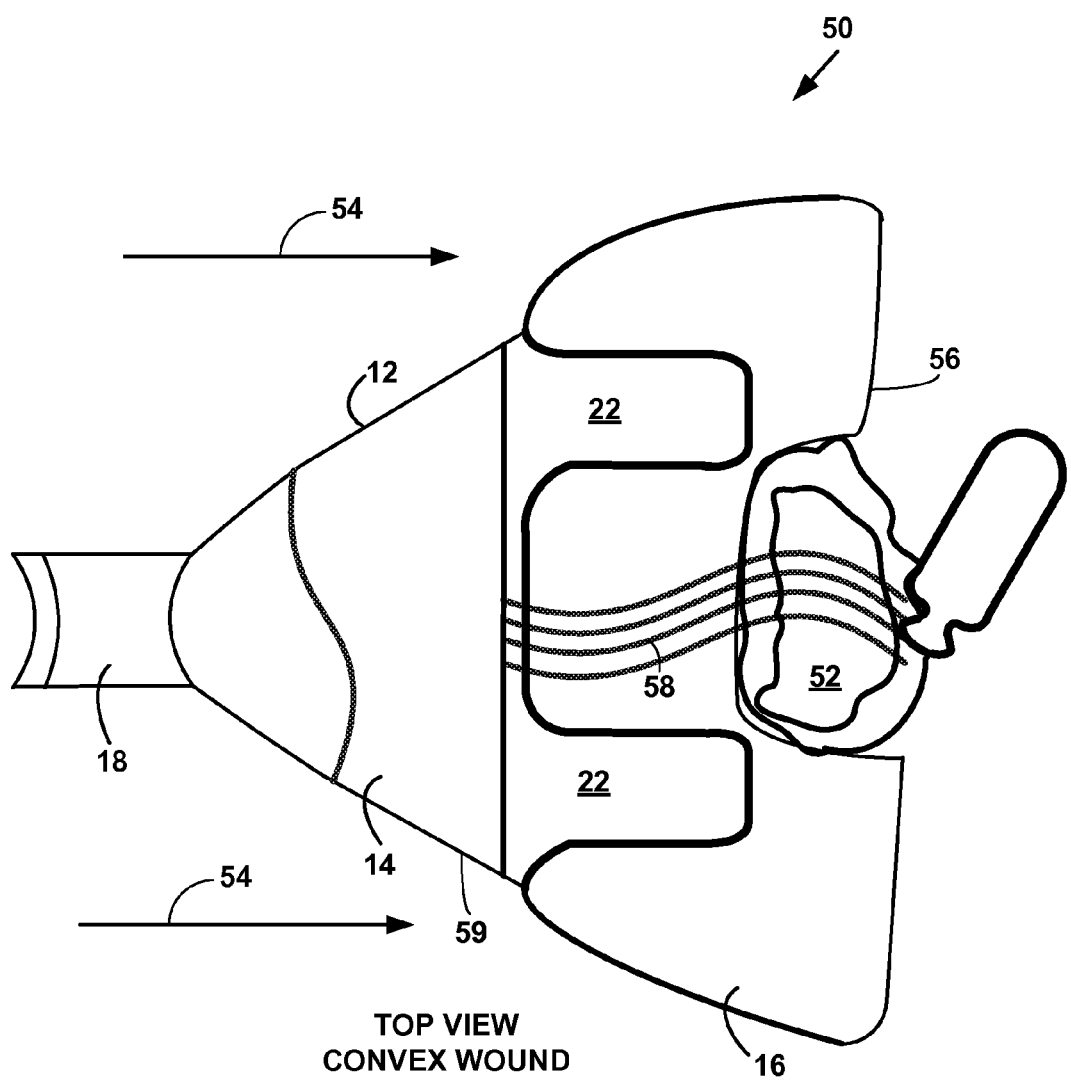
FIG. 5 is a block diagram illustrating another top view of the disposable partially flexible surgical fluid container apparatus pressed against a wound.

FIG. 5 is a block diagram illustrating another top view 50 of the disposable partially flexible surgical fluid container apparatus 12 pressed against a convex wound 52. In FIG. 5, when a forward force 54 is placed on the apparatus 12, a front surface 56 of the flexible sealing portion 16 is deformed and conformed to an edge surface of the convex wound 52 to form a seal allowing collection of irrigation fluids 58 in the rigid fluid collection portion 14 without leaking.

Figure 6:
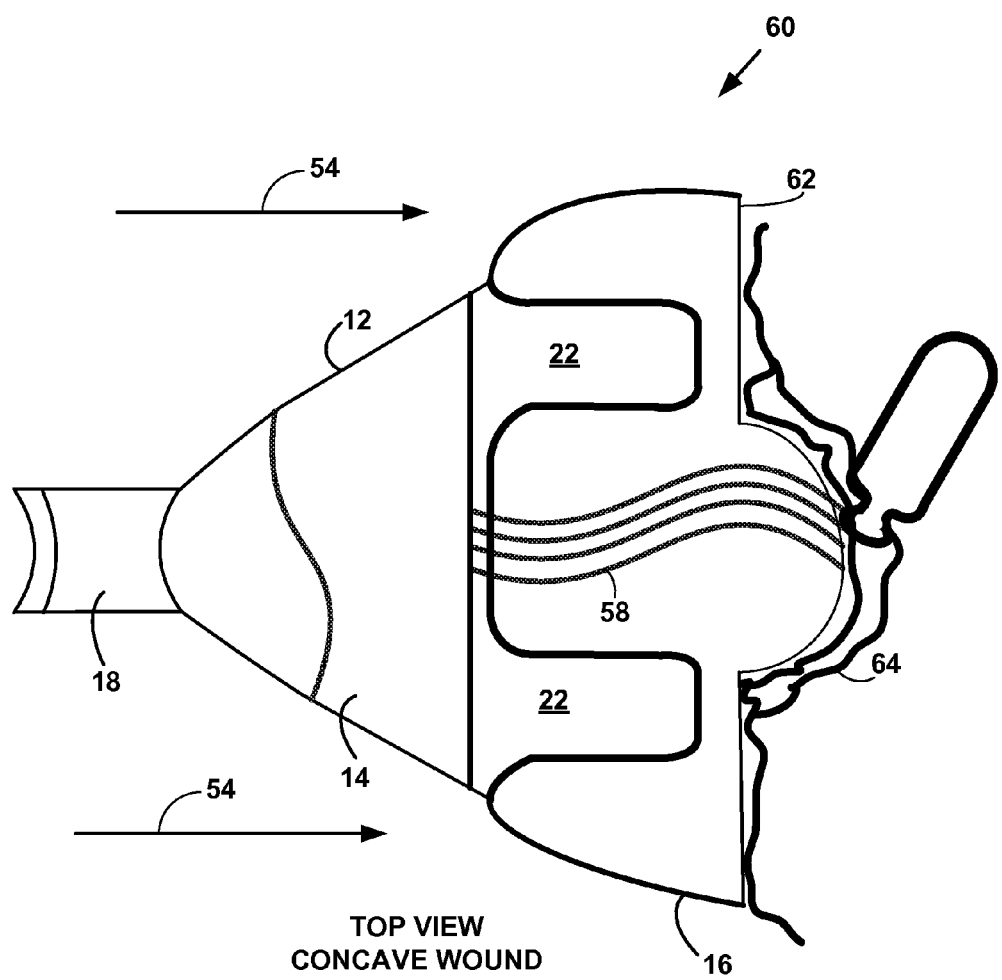
FIG. 6 is a block diagram illustrating another top view of the of the disposable partially flexible surgical fluid container apparatus pressed against a concave wound.

FIG. 6 is a block diagram illustrating another top view 60 of the of the disposable partially flexible surgical fluid container apparatus 12 pressed against a concave wound 62. In FIG. 6, when a forward force 54 is placed on the apparatus 12, a front surface 64 of flexible sealing portion 16 is deformed and conformed into a concave opening to an edge surface of the concave wound 62 to form a seal allowing collection of irrigation fluids 58 in the rigid fluid collection portion 14 without leaking.

Figure 7:
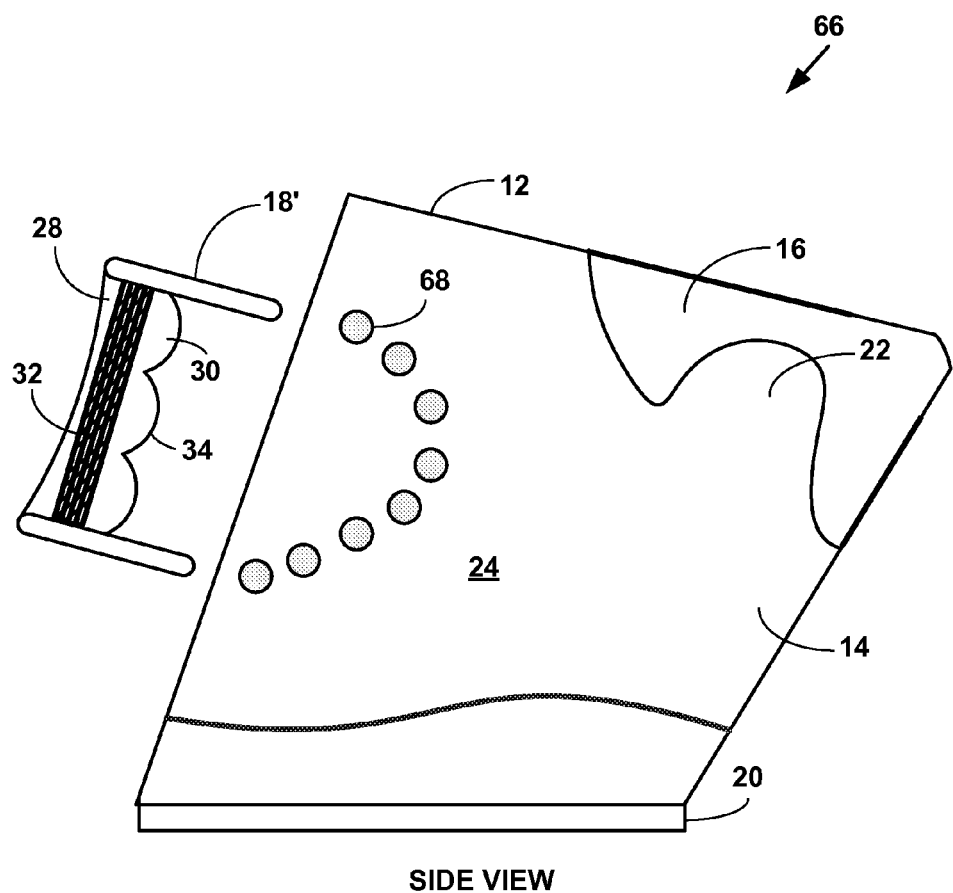
FIG. 7 is a block diagram illustrating a side view of a disposable partially flexible surgical fluid container apparatus with an adjustable handle.

FIG. 7 is a block diagram illustrating another side view 66 of a disposable partially flexible surgical fluid container apparatus 12 with an adjustable handle 18. FIG. 7 illustrates an adjustable handle 18' adjustable by insertion and removing into various insertion components 68 (not drawn to scale or at the proper angles to illustrate details) integral to rigid fluid collection portion 14 on plural sides to provide a desired handle angle.

Figure 8:
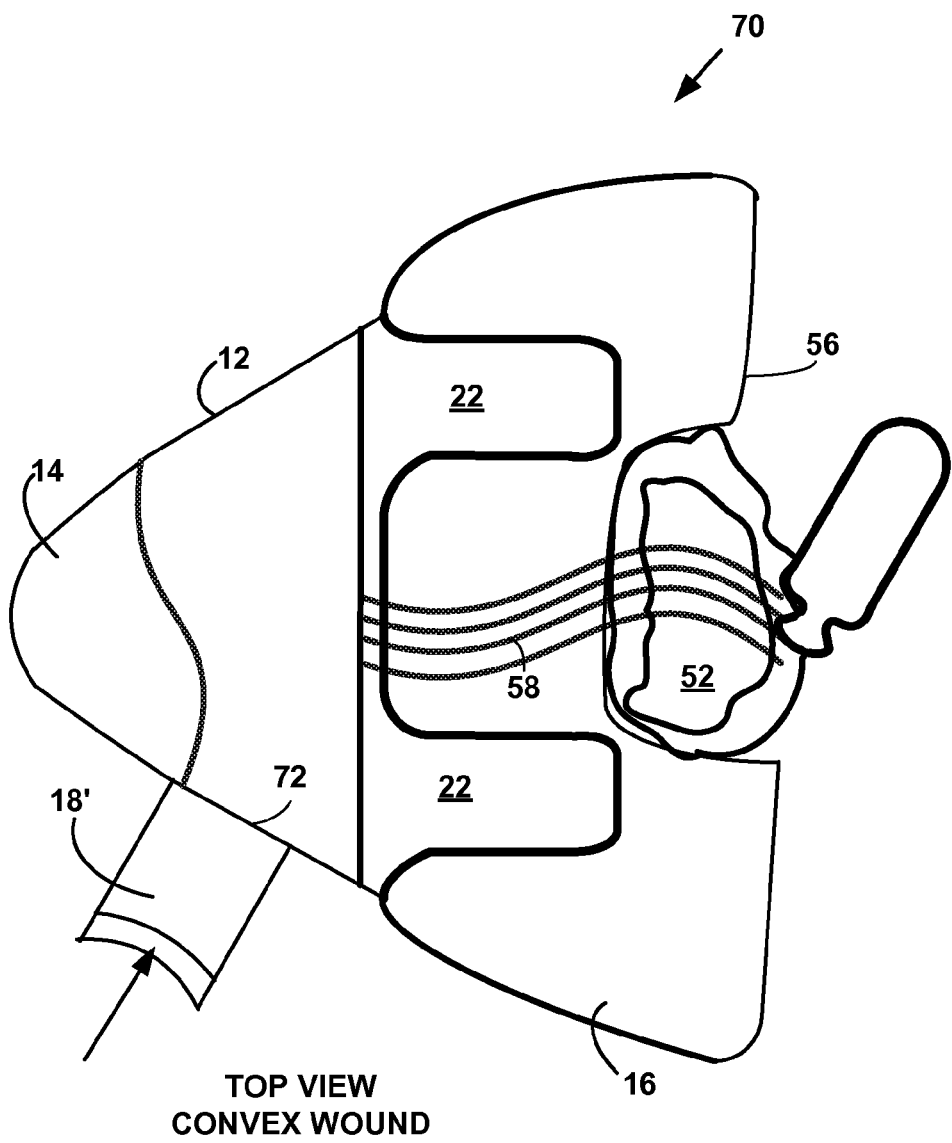
FIG. 8 is a block diagram illustrating another top view of the of the disposable partially flexible surgical fluid container apparatus pressed against a concave wound with the ergonomic handle in a corner position.

FIG. 8 is a block diagram illustrating another top view 72 of the of the disposable partially flexible surgical fluid container apparatus 12 pressed against the concave wound 62 with the adjustable ergonomic handle 18 in a corner position 72 on the rigid fluid collection portion 14. The corner position 72 allows a focused and specified force via the handle 18.

In one embodiment, the adjustable handle 18' can be moved to a corner portion 72 of the apparatus 12 to provide an angled force for a specific type of concave or convex wound.

However, the present invention is not limited to such an embodiment and more, fewer or other types of embodiments can be used to provide an adjustable handle 18 to practice the invention.

The whole apparatus 12 and/or separate components thereof may be injection molded, extruded, pultruded, pullwinded and/or manufactured and/or produced with other techniques. However, the present invention is not limited to such an embodiment and more, fewer or other types manufacturing techniques can be used to practice the invention.

"Extrusion" is a manufacturing process where a material is pushed through a die to create long objects of a fixed cross-section. Hollow sections are usually extruded by placing a pin or mandrel in the die. Extrusion may be continuous (e.g., producing indefinitely long material) or semi-continuous (e.g., repeatedly producing many shorter pieces). Some extruded materials are hot drawn and others may be cold drawn.

Feedstock for extrusion may be forced through the die by various methods: by an auger, which can be single or twin screw, powered by an electric motor; by a ram, driven by hydraulic pressure, oil pressure or in other specialized processes such as rollers inside a perforated drum for the production of many simultaneous streams of material.

"Pultrusion" is a continuous process for manufacture of materials with a constant cross-section. Reinforced fibers are pulled through a resin, possibly followed by a separate pre-forming system, and into a heated die, where the resin undergoes polymerization. Pultrusion is not limited to thermosetting polymers or polymides. More recently, pultrusion has been successfully used with thermoplastic matrices such either by powder impregnation of fibers or by surrounding it with sheet material of a thermoplastic/polymide matrix, which is then heated.

In one embodiment, components of the apparatus 12 are produced with an overwrapping transverse winding process that combines continuous filament winding with a pultrusion manufacturing process to produce a pultruded pullwound hollow cylindrical structure with the shape of hollow cylindrical structure that is used for components in apparatus 12.

The "pullwinding" process incorporates plural longitudinal reinforcement fibers with plural helical-wound (e.g., hoop, etc.) layers, providing maximum torsional properties and hoop strength. A self-contained inline winding unit is used with a pultrusion machine for feeding angled fibers between layers of unidirectional fibers before curing in a pultrusion die. The plural longitudinal re-enforcement fibers are used for axial and bending resistance while the plural helical-wound fibers are used for hoop tension and compression resistance. The pullwinding equipment is comprised of twin winding heads which revolve in opposite directions over a spindle. However, the present invention is not limited to such an embodiment and other embodiments can also be used to practice the invention.

In another embodiment, the apparatus 12 components other than the flexible sealing portion 16, is constructed from surgical stainless steel, other metals, other plastics, ceramics, composite material and/or other materials, and/or combination thereof and is re-usable, autoclavable and sterilizable.

In one embodiment, the apparatus 12 components, other than flexible sealing portion 16, are cast and includes zirconium dioxide ($ZrO_2$; also known as zirconia) and other types of ceramics. Ceramic containers 12 will not corrode in harsh surgical environments, are non-magnetic, and do not conduct electricity. Because of their resistance to strong acid and caustic substances. However, the present invention is not limited to such an embodiment and other embodiments can also be used to practice the invention.

In one embodiment, apparatus 12 is an integral, one-time use, disposable apparatus and is constructed from the plastic materials described above. The apparatus 12 is constructed from an economical material (various plastics described above) and is intended to be a single-use, disposable apparatus. The apparatus 12 comes in a sterile package that is opened and used during a surgery. When the surgery is finished, the apparatus 12 is thrown away.

In another embodiment, the apparatus 12, other than flexible sealing portion 16, is constructed from surgical stainless steel, other metals, plastic, ceramic composite material and/or other materials, and/or combination thereof and is re-usable, autoclavable and sterilizable.

In another embodiment, the flexible sealing portion 16, is a removable/insertable one-time use, disposable component and is constructed from the materials described above. In this embodiment, the rest of the apparatus 12 is constructed from surgical stainless steel, other metals, plastic, ceramic composite material and/or other materials, and/or combination thereof and is re-usable, autoclavable and sterilizable.

There are other various combinations of components of the apparatus 12 that can be used to practice the invention using the materials described above to make the whole apparatus or portions thereof single-use and disposable and surgical stainless steel, other metals, plastic, ceramic composite material and/or other materials, and/or combination thereof can be used to make the whole apparatus 12 or portions thereof re-usable, autoclavable and sterilizable.

The apparatus 12 was described for use with surgery for humans. However, the apparatus 12 can also be used for surgery on animals (or plants, etc.) and is not limited to surgery for humans. The apparatus 12 can also be used for non-surgical applications such as catching washing fluids in a machine shop, mechanic shop, oil change shop, etc.

The apparatus 12 significantly collecting irrigation fluids during surgery without spilling or leaking.

It should be understood that the architecture, processes, methods apparatus and devices described herein are not related or limited to any particular type of materials or design unless indicated otherwise. Various types of materials and designs may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams that describe any devices.

While various elements of the preferred embodiments have been specifically described as being implemented in specific designs and materials, in other embodiments other designs and materials may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

I claim:

1. A disposable partially flexible surgical fluid catching container apparatus, comprising in combination:
    a triangular shaped portion including a rigid fluid collection portion for storing fluids, a flexible sealing portion for catching surgical fluids, an ergonomic handle portion for grasping and holding and a horizontal bottom portion;
    the rigid fluid collection portion including a rigid material for collecting surgical fluids from a wound during a surgery, the rigid fluid collection portion including a plurality of rigid protrusions protruding into the flexible sealing portion providing additional surfaces for applying pressure and control in holding the flexible sealing portion against a wound surface, the rigid fluid collection portion including a plurality of trapezoid shaped sides oriented at a pre-determined angle from the horizontal bottom portion;
    the plurality of rigid protrusions including a first rigid surface connected to the rigid fluid connection portion and one or more other rigid surfaces connected to and protruding into the flexible sealing portion, a combination of the plurality of rigid protrusions and the flexible sealing portion forming a smooth integral surface portion of the apparatus, selected ones of the plurality rigid protrusions forming a first rigid surface at a first end for applying a first pressure and control point for holding the flexible sealing portion against the wound surface and other selected ones of the plurality of rigid protrusions forming a second rigid surface at a second end applying a second pressure and control point for holding the flexible sealing portion against the wound surface, the plurality of rigid protrusions further applying pressure and control points for deforming and conforming the flexible sealing portion around a convex opening at an edge surface of a convex wound and for deforming and conforming the flexible sealing portion into a concave opening to an edge surface of a concave wound;
    the flexible sealing portion attaching to the rigid fluid storage portion and including a flexible, conformable material for conforming to flat, convex and concave wound surfaces and creating a seal between the flexible sealing portion and the wound surfaces to prevent leaking of collected fluids, the flexible conformable material varying in thickness from a first greater thickness on a first part attached to the rigid fluid collection portion and a second lesser thickness a second part for conforming to flat, convex and concave wound surfaces;
    the ergonomic handle portion attaching to the rigid fluid collection portion at a pre-determined angle comprising a pre-determined pattern specifically sized and shaped for comfortable gripping by a human hand, the pre-determined angle allowing accurate collecting of fluids into the flexible sealing portion from a wound during the surgery; and
    the horizontal bottom portion for standing the apparatus upright when placed on a flat surface.

2. The disposable partially flexible surgical fluid catching container apparatus of claim 1 wherein the rigid fluid storage portion includes polyetherimide, polyimide, other thermosetting polyimides or rigid composite materials.

3. The disposable partially flexible surgical fluid catching container apparatus of claim 1 wherein the flexible sealing portion includes polyvinyl chloride (PVC) polyethylene, polypropylene, very low-density polyethylene (VLDPE), linear low-density polyethylene (LLDPE), flexible polypropylene (FPP), ethylene interpolymer alloy (EIA), ethylene propylene diene monomer (EPDM), or flexible composite materials.

4. The disposable partially flexible surgical fluid catching container apparatus of claim 1 wherein at least any one portion of the rigid fluid collection portion is oriented from the horizontal bottom portion at a pre-determined angle of twenty to sixty degrees.

5. The disposable partially flexible surgical fluid catching container apparatus of claim 1 wherein the flexible conformable material varies in thickness from fifty millimeters at the first greater part down to one millimeter at the second lesser part.

6. The disposable partially flexible surgical fluid catching container apparatus of claim 1 wherein the ergonomic handle includes a wave pattern shape or a twisted spiral shape for comfortably engaging human fingers.

7. The disposable partially flexible surgical fluid catching container apparatus of claim 1 wherein the ergonomic handle is attached to the rigid fluid collection container at fixed angle of one degree to an angle of forty five degrees.

8. The disposable partially flexible surgical fluid catching container apparatus of claim 1 wherein horizontal bottom portion includes a weighted portion for standing the apparatus upright when placed on a flat surface when filled with fluids collected from a surgery.

9. The disposable partially flexible surgical fluid catching container apparatus of claim 1 wherein the apparatus is created by an injection molding, extruding, pultruding or pull winding process.

10. The disposable partially flexible surgical fluid catching container apparatus of claim 1 wherein apparatus is an integral, single-use, disposable apparatus.

11. A partially flexible surgical fluid catching container apparatus, comprising in combination:

a triangular shaped portion including a rigid fluid collection portion for storing fluids, a removable and re-attachable flexible sealing portion for catching surgical fluids, a manually configurable ergonomic handle portion for grasping and holding and a horizontal bottom portion, wherein the manually configurable ergonomic handle portion is manually removable and re-attachable to any of a plurality of sides of the triangular shaped portion at any of a plurality of different gripping angles;

the rigid fluid collection portion including a rigid material for collecting surgical fluids from a wound during a surgery, the rigid fluid collection portion including a plurality of rigid protrusions protruding into the flexible sealing portion providing additional surfaces for applying pressure and control in holding the removable and re-attachable flexible sealing portion against a wound surface, the rigid fluid collection portion including a plurality of trapezoid shaped sides oriented at a pre-determined angle from the horizontal bottom portion;

the plurality of rigid protrusions including a first rigid surface connected to the rigid fluid connection portion and one or more other rigid surfaces connected to and protruding into the removable and re-attachable flexible sealing portion, a combination of the plurality of rigid protrusions and the removable and re-attachable flexible sealing portion forming a smooth integral surface portion of the apparatus, selected ones of the plurality rigid protrusions forming a first rigid surface at a first end for applying a first pressure and control point for holding the removable and re-attachable flexible sealing portion against the wound surface and other selected ones of the plurality of rigid protrusions forming a second rigid surface at a second end applying a second pressure and control point for holding the removable and re-attachable flexible sealing portion against the wound surface, the plurality of rigid protrusions further applying pressure and control points for deforming and conforming the removable and re-attachable flexible sealing portion around an edge surface of a convex opening of a convex wound and for deforming and conforming the removable and re-attachable flexible sealing portion into a concave opening to an edge surface of a concave wound;

the removable and re-attachable flexible sealing portion attaching to the rigid fluid storage portion and including a flexible, conformable material for conforming to flat, convex and concave wound surfaces and creating a seal between the removable and re-attachable flexible sealing portion and the wound surfaces to prevent leaking of collected fluids, the flexible conformable material varying in thickness from a first greater thickness on a first part attached to the rigid fluid collection portion and a second lesser thickness a second part for conforming to flat, convex and concave wound surfaces;

the manually configurable ergonomic handle portion attaching to the rigid fluid collection portion at a pre-determined angle comprising a pre-determined pattern specifically sized and shaped for comfortable gripping by a human hand, the pre-determined angle allowing accurate collecting of fluids into the flexible sealing portion from a wound during the surgery; and the horizontal bottom portion for standing the apparatus upright when placed on a flat surface.

12. The partially flexible surgical fluid catching container apparatus of claim 11 wherein the rigid fluid storage portion includes polyetherimide, polyimide, other thermosetting polyimides or rigid composite materials.

13. The partially flexible surgical fluid catching container apparatus of claim 11 wherein the removable and re-attachable flexible sealing portion includes polyvinyl chloride (PVC) polyethylene, polypropylene, very low-density polyethylene (VLDPE), linear low-density polyethylene (LLDPE), flexible polypropylene (FPP), ethylene interpolymer alloy (EIA), ethylene propylene diene monomer (EPDM), or flexible composite materials.

14. The partially flexible surgical fluid catching container apparatus of claim 11 wherein the removable and re-attachable flexible sealing portion is removable and re-attachable with a snap connection means or a magnetic connection means.

15. The partially flexible surgical fluid catching container apparatus of claim 11 wherein the removable and re-attachable flexible sealing portion includes a plurality of different sizes and shapes.

16. The partially flexible surgical fluid catching container apparatus of claim 11 wherein the manually configurable ergonomic handle is manually configurable from an angle of one degree to an angle of forty five degrees.

17. The partially flexible surgical fluid catching container apparatus of claim 11 wherein components of the apparatus other than flexible sealing portion are constructed from surgical stainless steel, other metals, ceramics, composite material or combinations thereof and is re-usable, autoclavable and sterilizable.

* * * * *